(12) United States Patent
Minato et al.

(10) Patent No.: US 6,692,476 B1
(45) Date of Patent: Feb. 17, 2004

(54) DISPOSABLE DIAPER

(75) Inventors: Hironao Minato, Kagawa-ken (JP); Yasushi Sayama, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 0 days.

(21) Appl. No.: 09/607,634

(22) Filed: Jun. 30, 2000

(30) Foreign Application Priority Data

Jul. 1, 1999 (JP) ............................................. 11-188080

(51) Int. Cl.[7] ................................................ A61F 13/15
(52) U.S. Cl. ............................ 604/385.27; 604/385.22; 604/385.24; 604/385.01
(58) Field of Search ........................ 604/385.01, 385.03, 604/385.22, 385.24, 385.27, 385.3, 394, 396

(56) References Cited

U.S. PATENT DOCUMENTS 5,370,634 A  * 12/1994  Ando et al. ............... 604/385.1
6,142,985 A  * 11/2000  Feist ...................... 604/385.28

FOREIGN PATENT DOCUMENTS

| JP | A 9-103448 | 4/1997 |
| WO | WO 95/12374 | 5/1995 |
| WO | WO 99/00095 | 1/1999 |

* cited by examiner

*Primary Examiner*—Weilun Lo
*Assistant Examiner*—Jacqueline Stephens
(74) *Attorney, Agent, or Firm*—Butzel Long

(57) ABSTRACT

A disposable diaper including a laminated panel that includes a liquid-pervious topsheet, a liquid-impervious backsheet and a liquid-absorbent core disposed therebetween. Side flaps of the panel are provided with leg-opening elastic members rectilinearly extending longitudinally thereof between the front and rear waist regions and secured under tension to the respective side flaps, the rear waist regions of the panel is provided between the respective side edges of the core and the respective leg-opening elastic members with a pair of stretchable regions being elastically stretchable transversely of the panel.

3 Claims, 5 Drawing Sheets

DISPOSABLE DIAPER

BACKGROUND OF THE INVENTION

This invention relates to a disposable diaper for absorbing and containing excretion.

Japanese Patent Application Disclosure No. 1997-103448 describes a disposable diaper comprising a liquid-pervious topsheet, a liquid-impervious backsheet and a liquid-absorbent core disposed between these sheets. The diaper further comprises a pair of side flaps extending outward beyond transversely opposite side edges of the core and elastic members extending longitudinally of the diaper to be associated with respective leg-openings which are secured under tension to the respective side flaps.

In the case of this diaper described, the side flaps are curved inward transversely of the diaper and the leg-opening elastic members rectilinearly extend between front and rear waist regions longitudinally of the diaper. With this diaper put on the wearer, the respective leg-opening elastic members extending between the front and rear waist regions can not form closed loops around respective thighs of the wearer. Consequently, it is concerned that undesirable gaps might be left between the wearer's thighs and the respective side flaps and excretion might leak through these gaps.

SUMMARY OF THE INVENTION

It is an object of this invention to provide a disposable diaper enabling the leg-opening elastic members rectilinearly extending between the front and rear waist regions longitudinally of the diaper to form the closed loops around the wearer s thighs as the diaper is put on the wearer and thereby to prevent any amount of excretion from leaking along the wearer's thighs.

According to this invention, there is provided a disposable diaper in the form of a laminated panel comprising a liquid-pervious topsheet, a liquid-impervious backsheet and a liquid-absorbent core disposed therebetween to define a front waist region, a rear waist region and a crotch region extending therebetween, and the panel being provided with a pair of side flaps that transversely extends outward beyond transversely opposite side edges of the core and that extends longitudinally of the panel and the side flaps being provided with leg-opening elastic members that rectilinearly extend longitudinally thereof between the front and rear waist regions and that are secured under tension to respective the side flaps; wherein at least one of the front and rear waist regions is provided between respective said side edges of the core and respective said leg-opening elastic members with a pair of stretchable regions which are elastically stretchable at least transversely of the panel.

The disposable diaper according to this invention enables the leg-opening elastic members to be curved outward transversely of the panel as the stretchable regions formed on the panel are stretched outward transversely of the panel even though the stretchable regions rectilinearly extend longitudinally of the panel before the panel is put on a the wearer. Consequently, the panel can be put on the wearer so that the respective leg-opening elastic members may form substantially closed loop and reliably surround the wearer's thighs. In this manner, it is not concerned that any undesirable gaps might be left between the side flaps and the wearer's thighs and any amount of excretion might leak along the wearer's thighs.

DETAILED DESCRIPTION OF THE PREFERRED EMBODIMENTS

Details of a disposable diaper according to this invention will be more fully understood from the description given hereunder in reference with the accompanying drawings.

Figure 1:
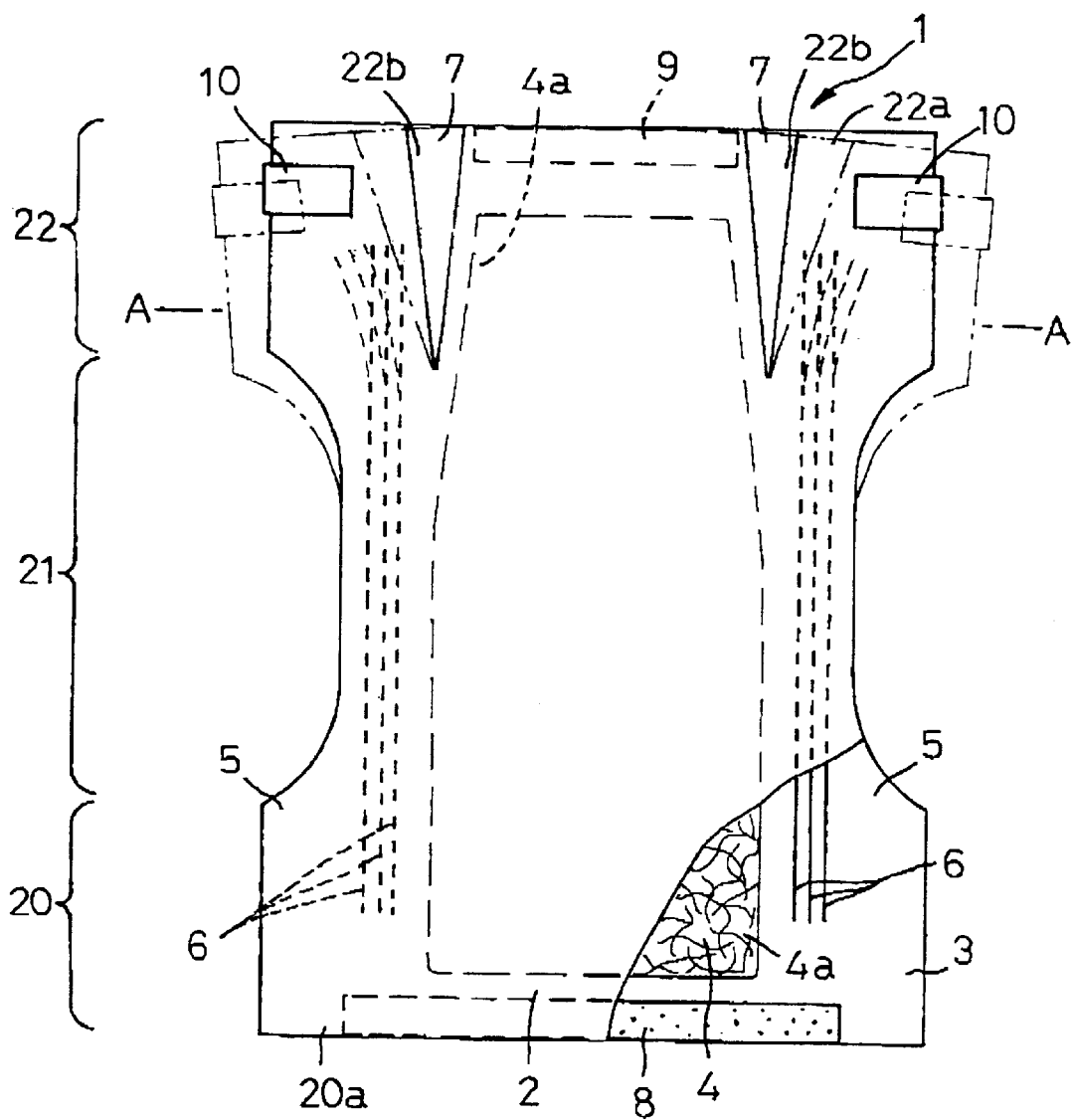
FIG. 1 is a partially cutaway plan view showing a disposable diaper according to a principle of this invention.

FIG. 1 is a partially cutaway plan view showing the disposable diaper of this invention, in which imaginary lines indicate a rear waist region stretched outward transversely of the diaper. The diaper is in the form of a laminated panel 1 comprising a liquid-pervious topsheet 2, a liquid-impervious backsheet 3 and a liquid-absorbent core 4 disposed between these sheets 2, 3 and joined to the inner surface of at least one of these sheets 2, 3. The diaper is longitudinally composed of a front waist region 20, a rear waist region 22 and a crotch region 21 extending between the front and rear waist regions 20, 22.

The panel 1 is provided with a pair of side flaps 5, 5 transversely extending outward beyond transversely opposite side edges 4a, 4a of the core 4 and extending longitudinally of the panel 1. In the crotch region 21, the respective side flaps 5, 5 are curved inward transversely of the panel 1 The side flaps 5, 5 are respectively provided with elastic members 6, 6 rectilinearly extending longitudinally of the panel 1 to be associated with leg-openings and disposed between the top- and backsheets 2, 3. The elastic members 6, 6 are secured under tension to the inner surface of at least one of these sheets 2, 3.

The rear waist region 22 of the panel 1 is formed with a pair of V-shaped cutouts 22b (stretchable regions) lying between the respective side edges 4a, 4a of the core 4 and the respective leg-opening elastic members 6, 6 and longitudinally extending from a longitudinally outer end 22a of the rear waist region 22 to the vicinity of the crotch region 21. A pair of elastically stretchable members 7, 7 which are stretchable transversely as well as longitudinally of the panel 1 are secured under no tension to the panel 1 so as to cover the respective cutouts 22b.

The panel 1 is further provided along longitudinally outer ends 20a, 22a of the front and rear waist regions 20, 22 with transversely extending film-like elastic members 8, 9 associated with a waist-opening. The elastic members 8, 9 are disposed between the top- and backsheets 2, 3 and secured under tension to the inner surface of at least one of these sheets 2, 3. The rear waist region 22 of the panel 1 is provided with a pair of tape fasteners 10 having their proximal ends fixed to the panel 1 and extending inward from transversely opposite side edges of the rear waist region 22.

The elastic members 7, 7 are stretched transversely outward as the rear waist region 22 is developed transversely outward with free ends of the respective tape fasteners 10 held between the fingers. The leg-opening elastic members 6, 6 rectilinearly extending in the rear waist region 22 are curved outward transversely of the panel 1 as indicated by the imaginary lines in FIG. 1 as the elastic members 7, 7 are stretched. Such feature enables the panel 1 to be put on the wearer with the respective leg-opening elastic members 6, 6 forming substantially closed loops around the wearer's thighs.

Figure 2:
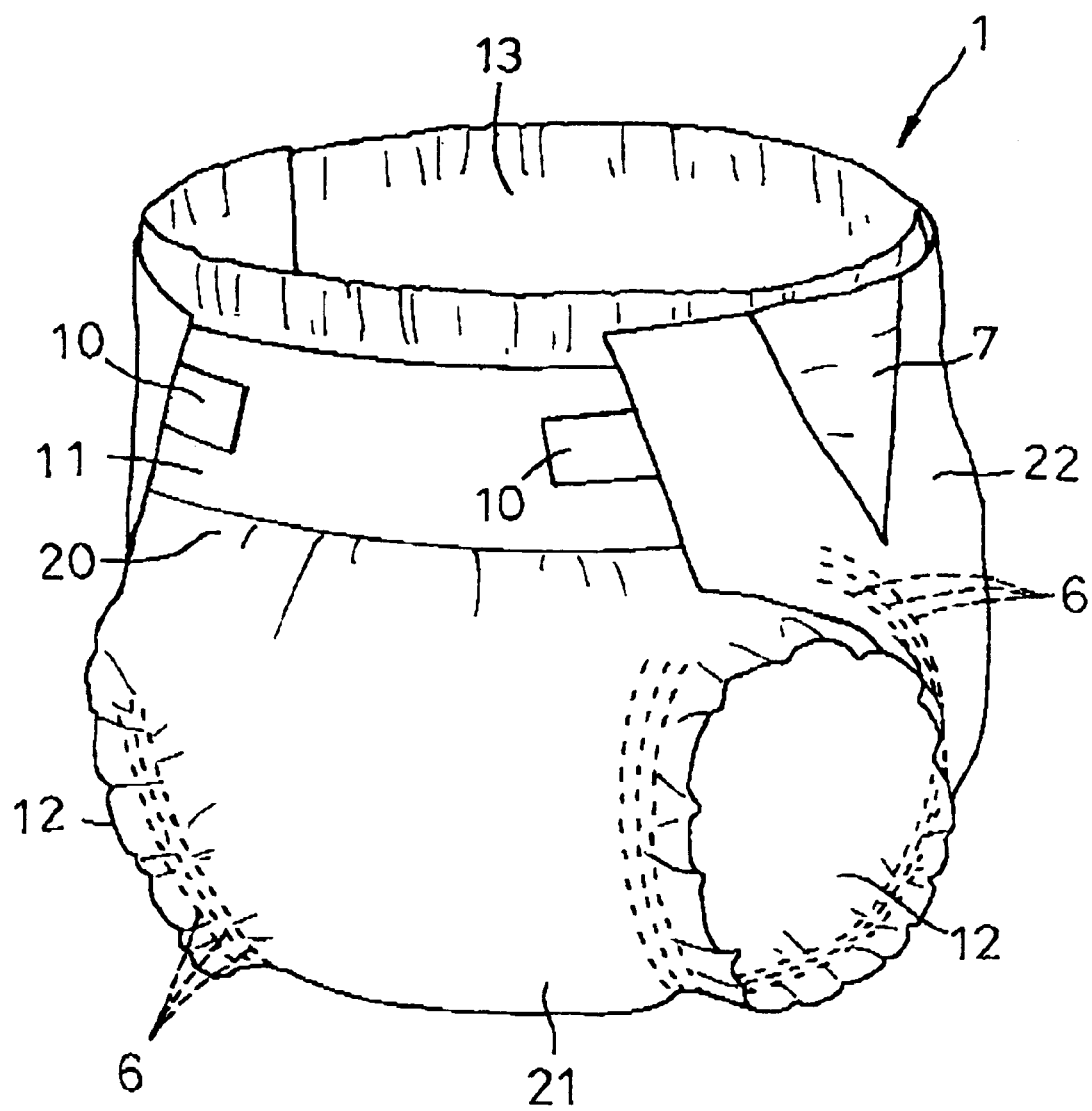
FIG. 2 is a perspective view showing the diaper as assembled.

FIG. 2 is a perspective view showing the diaper in its assembled state. In the front waist region 20, the panel 1 is provided on its outer surface with pieces of target tape 11 on which the respective tape fasteners 10 are anchored. The tape fasteners 10 may be anchored on the respective pieces of target tape 11 by means of pressure sensitive adhesive applied on inner surfaces of the respective tape fasteners' free ends to form the pair of leg-openings 12 and the waist-opening 13. Referring to FIG. 2, the leg-opening elastic members 6, 6 extend to describe substantially closed loops and the panel 1 is formed along the leg-openings 12 as well as the waist-opening 13 with gathers due to the contraction of the elastic members 6, 6, 8, 9.

Figure 3:
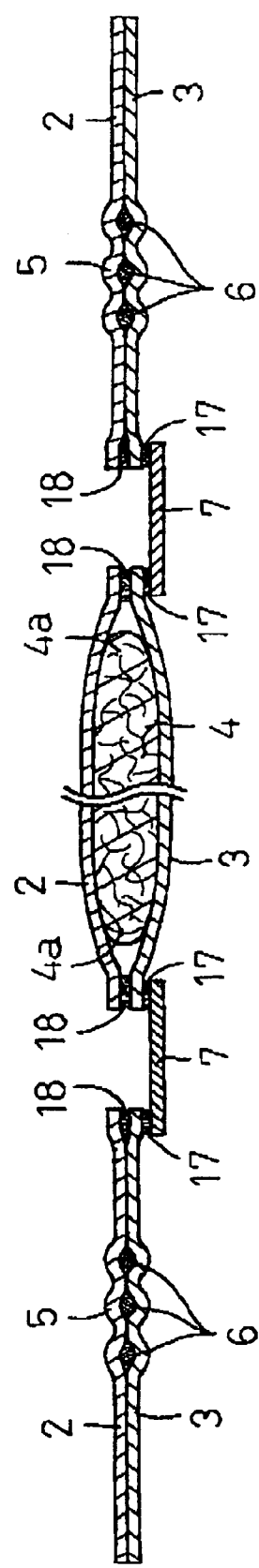
FIG. 3 is a sectional view taken along line A—A in FIG. 1.

FIG. 3 is a sectional view taken along line A—A in FIG. 1, showing a transversely middle zone of the diaper as partially eliminated. The elastic members 7, 7 are secured along their peripheral edges to the outer surface of the backsheet 3 by means of adhesive 17 and, in the vicinity of the peripheral edges of the respective elastic members 7, 7, the respective inner surfaces of the top- and backsheets 2, 3 are joined to each other by means of adhesive 18.

The side flaps 5, 5 are formed by portions of the top- and backsheets 2, 3 transversely extending outward beyond the side edges 4a, 4a of the core 4 and joined together.

Figure 4:
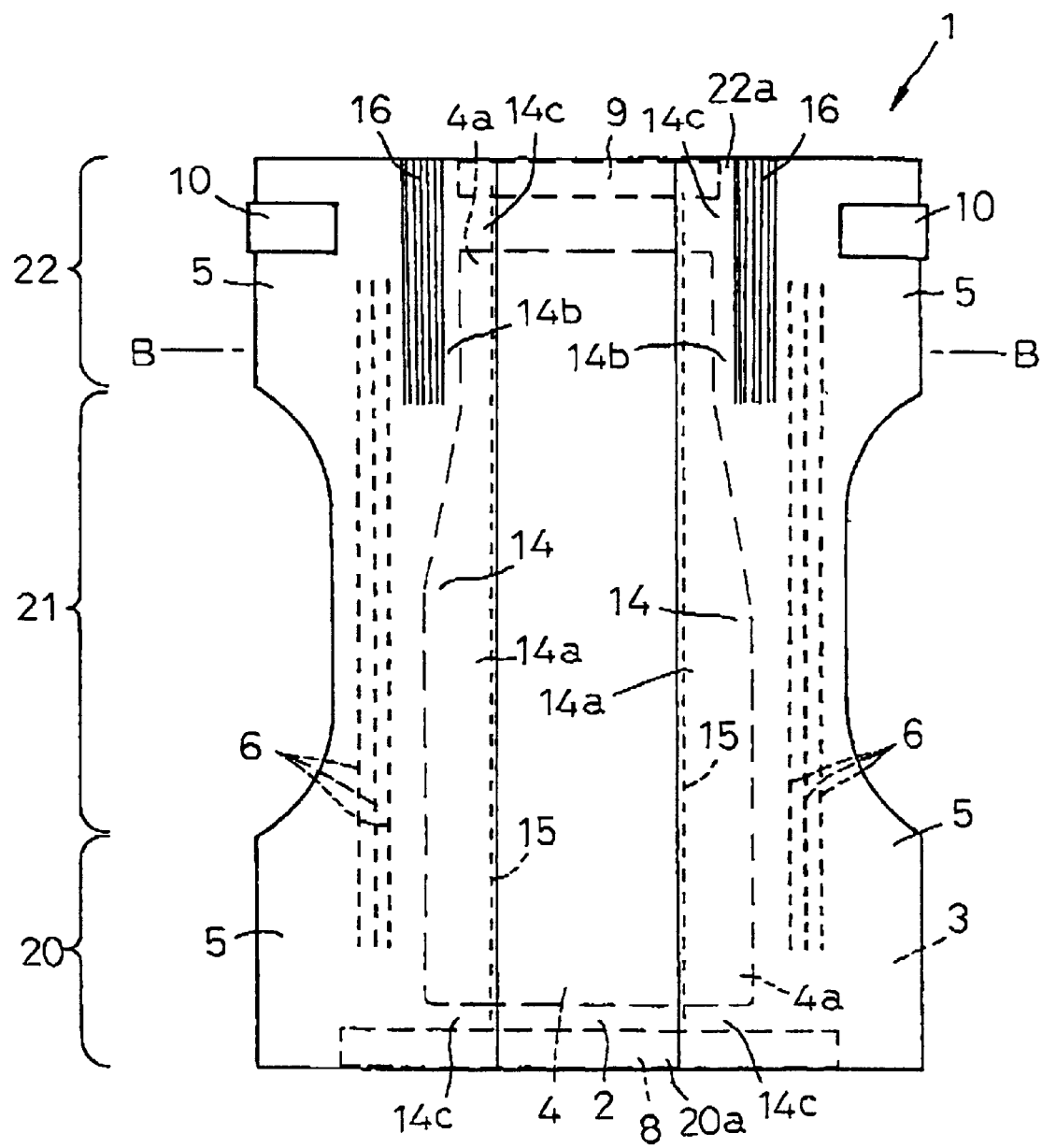
FIG. 4 is a view similar to FIG. 1 but showing another preferred embodiment of the disposable diaper according to this invention.

FIG. 4 is a view similar to FIG. 1 but showing another preferred embodiment of the diaper according to this invention. This diaper is similar to the diaper of FIG. 1 in that the diaper is in the form of the laminated panel 1 comprising the top- and backsheets 2, 3 and the core 4 disposed between these sheets 2, 3 and the panel 1 further includes the pair of side flaps 5, 5 provided with the rectilinear leg-opening elastic members 6, 6 extending longitudinally of the panel 1.

In the rear waist region 22, the panel 1 is formed with a pair of pleated regions 16, 16 (stretchable regions). The pleated regions 16, 16 lie between the side edges 4a, 4a of the core 4 and the respective leg-opening elastic members 6, 6 and extend to the vicinity of the crotch region. The pleated regions 16, 16 are stretchable transversely of the panel 1 (not shown).

The panel 1 is provided on its inner surface with a pair of leakage cuffs 14, 14 lying between the side edges 4a, 4a of the core 4 and the respective leg-opening elastic members 6, 6 and extending longitudinally of the panel 1. Each of the cuffs 14, 14 comprises a free edge 14a joined neither to the topsheet 2 nor to the backsheet 3 in the crotch region 21, fixed proximal edge 14b extending longitudinally of the panel 1, and longitudinally opposite ends 14c, 14c lying in the front and rear waist regions 20, 22, respectively, and joined, as they are collapsed inwardly of the panel 1, to the outer surface of the topsheet 2. The portion of the cuff 14 extending transversely outward from the fixed proximal edge 14b and the longitudinally opposite ends 14c, 14c have the same configuration as that of the backsheet 3 extending transversely outward beyond the side edges 4a, 4a of the core 4. The cuff 14 is provided along its free edge 14a with an elastic member 15 extending longitudinally thereof and secured under tension to the cuff 14.

Figure 5:
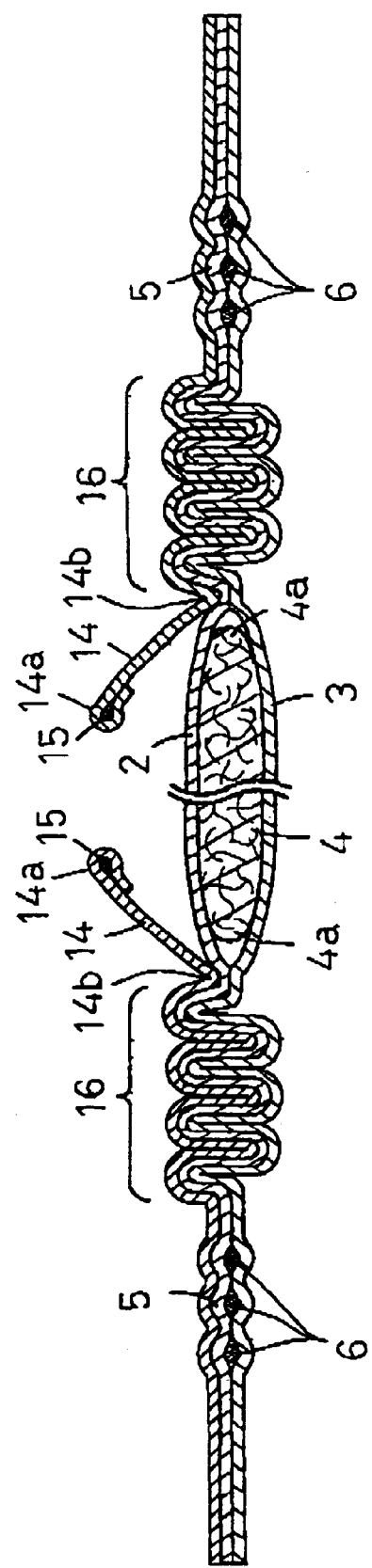
FIG. 5 is a sectional view taken along line B—B in FIG. 4.

FIG. 5 is a sectional view taken along line B—B in FIG. 4, showing a transversely middle zone of the diaper as partially eliminated. The pleated regions 16, 16 are formed by the portions of the top- and backsheets 2, 3 extending transversely outward beyond the side edges 4a, 4a of the core 4 together with the portions of the cuffs 14, 14 extending transversely outward beyond the side edges 4a, 4a of the core 4 and extend transversely outward from the side edges 4a, 4a of the core 4 in undulation.

The side flaps 5, 5 are formed by the portions of the top- and backsheets 2, 3 extending transversely outward beyond the side edges 4a, 4a of the core 4 and the portions of the cuffs 14, 14.

The cuffs 14 are joined along their fixed proximal edges 14b, 14b to the outer surface of the topsheet 2. The free edges 14a, 14a of the cuffs 14, 14 are bent inwardly of the panel 1 to wrap elastic members 15, 15 secured thereto, respectively. These elastic members 15, 15 contract and the cuffs 14, 14 rise (not shown) on the inner surface of the panel 1 as the latter is longitudinally curved with its inner surface inside.

The pleated regions 16, 16 are rectilinearly stretched transversely outward as the rear waist region 22 is stretched transversely outward with free ends of the respective tape fasteners 10 held between the fingers. The elastic members 6, 6 associated with the leg-openings rectilinearly extending in the rear waist region 22 are curved outward transversely of the panel 1 as the pleated regions 16, 16 are stretched. Such feature enables the panel 1 to be put on the wearer with the respective leg-opening elastic members 6, 6 forming substantially closed loops around the wearer's thighs.

The rear waist region 22 of the panel 1 is stretched transversely outward of the panel 1 by a stretched dimension of the pleated regions 16 and thereby enables the panel 1 to be put on the wearer having a relatively large waist size.

The topsheet 2 may be formed by a liquid-pervious, preferably liquid-pervious but hydrophobic sheet such as a nonwoven fabric or a porous plastic film. The backsheet 3 may be formed by a liquid-impervious plastic film or a laminated sheet consisting of a plastic film and a hydrophobic nonwoven fabric, preferably a breathable liquid-impervious sheet. The cuff 14 may be formed by a breathable nonwoven fabric, preferably a breathable liquid-impervious nonwoven fabric sheet. The nonwoven fabric may be selected from a group including a spun bond nonwoven fabric, a spun lace nonwoven fabric and a melt blown nonwoven fabric. The core 4 may be formed by a mixture of fluff pulp and highly absorptive polymer particles compressed to a desired thickness and covered with a liquid-pervious sheet such as tissue paper.

The elastically stretchable member 7 may be made of elastomer such as synthetic rubber or natural rubber or a nonwoven fabric on which the elastomer has been secured under tension. Joining of the core 4, the elastic members 6, 7, 8, 9, 15, sheets 2, 3 and the cuffs 14 may be carried out using hot melt adhesive, pressure sensitive adhesive or heat-sealing technique.

Alternatively, it is possible to form the panel 1 in its front and rear waist regions 20, 22 with the stretchable regions extending between the respective leg-opening elastic members 6, 6 and the respective side edges 4a, 4a of the core 4. It is also possible to form the panel 1 between the respective leg-opening elastic members 6, 6 and the respective side edges 4a, 4a of the core 4 with the stretchable regions extending between the longitudinal ends 20a, 22a of the front and rear waist regions 20, 22. The stretchable regions formed both in the front waist region 20 and in the rear waist region 22 enable the leg-opening elastic members 6, 6 lying in the rear waist region 22 as well as the leg-opening elastic members 6, 6 to be curved outward transversely of the panel because the front and rear waist regions 20, 22 are stretched outward transversely of the panel as the panel 1 is put on a wearer's body.

What is claimed is:

1. A disposable diaper comprising:
   a liquid-pervious topsheet;
   a liquid-impervious backsheet;
   a liquid-absorbent core disposed between the topsheet and the backsheet;
   a front waist region;
   a rear waist region;
   a crotch region extending between the front waist region and the rear waist region;
   a pair of side flaps that extend outward beyond transversely opposite side edges of said core and that further extend longitudinally of the diaper, said pair of side flaps being provided with elastic members that rectilinearly extend longitudinally between said front and rear waist regions and that are secured under tension to respective ones of said pair of side flaps; and
   a pair of stretchable regions provided in at least one of the front and rear waist regions between the side edges of the core and respective ones of the elastic members and spaced inward from a side edge of said at least one of the front and rear waist regions, the stretchable regions being triangular shaped and elastically stretchable at least transversely of said diaper, said elastic members being curved outward transversely of said diaper as said stretchable regions are stretched outward transversely of said diaper.

2. The diaper according to claim 1, wherein said side flaps are respectively curved inward transversely of said diaper in said crotch region.

3. The diaper according to claim 1, wherein said stretchable regions comprise elastically stretchable members that are inserted into spaces that extend longitudinally at least into a vicinity of the crotch region between the side edges of the core and respective ones of the elastic members.

* * * * *